United States Patent [19]
Taylor, Jr.

[11] 3,957,993
[45] May 18, 1976

[54] INHIBITION OF ULCERS WITH PYRROLYL-SUBSTITUTED PERIMIDINES
[75] Inventor: Russell J. Taylor, Jr., Palmyra, N.J.
[73] Assignee: McNeil Laboratories, Incorporated, Fort Washington, Pa.
[22] Filed: Dec. 12, 1974
[21] Appl. No.: 532,280

Related U.S. Application Data
[63] Continuation-in-part of Ser. No. 417,669, Nov. 20, 1973, abandoned.

[52] U.S. Cl. .............................................. 424/251
[51] Int. Cl.² ...................................... A61K 31/505
[58] Field of Search ..................... 424/251; 417/669

[56] References Cited
UNITED STATES PATENTS
3,502,647   3/1970   Paragamian ...................... 260/209

OTHER PUBLICATIONS
*Current Therapy* (1963), pp. 256–257.
*Text. of Org. Med. Chem. and Pharm. Chem.*, pp. 346–348.

*Primary Examiner*—Frederick E. Waddell

[57] ABSTRACT
The use of 2-pyrrolyl-perimidines as antiulcer agents.

2 Claims, No Drawings

INHIBITION OF ULCERS WITH PYRROLYL-SUBSTITUTED PERIMIDINES

REFERENCE TO PRIOR APPLICATION

This application is a continuation-in-part of a copending application Ser. No. 417,669, filed Nov. 20, 1973, now abandoned.

DESCRIPTION OF THE INVENTION

This invention relates to the use of certain known pyrrolyl-substituted perimidines (See U.S. Pat. No. 3,502,647) as an aid in the prevention and amelioration of stomach ulcers in man or animals. The subject perimidines may be structurally illustrated by the formula:

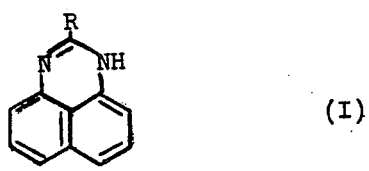

wherein R is a member selected from the group consisting of pyrrolyl and N-methylpyrrolyl. The pharmaceutically acceptable acid-addition salts of (I) are also included within the scope of this invention.

The subject 2-pyrrolyl-perimidines (I) and salts thereof are useful antiulcer agents as shown, for example, by their ability to inhibit gastric acid secretion and inhibit ulcer formation in standard laboratory animal tests. For example, antisecretory activity is observed in the 3-hour pyloric-ligated rat test at intraperitoneal (i.p.) or oral dose levels of about 10–100 mg/kg body weight.

The test procedure is a modification of the Shay et al. technique reported in Gastroenterology, 26, 906 (1954). Male Sprague-Dawley rats (CFE, 180–220 g), in individual cages, are allowed access solely to a solution of 8% sucrose and 0.2% sodium chloride ad libitum for 48 hours prior to administration of the compound to be tested. One hour after administration of the compound, the rat is anesthetized with ether, the pylorus is exposed by a mid-line laparotomy and tied off with surgical thread, and the incision is closed with autoclips. Three hours later the rat is sacrificed by cervical dislocation. The incision is reopened, the esophagus is clamped at the cardiac sphincter, and the entire stomach is excised. The stomach is cut open and the contents are allowed to drain into a centrifuge tube. The mucosa is washed with 2 ml of saline and the wash is added to the contents. The stomach contents are centrifuged at 600 × gravity for 30 minutes, after which the supernatant is decanted, mixed with 10 ml of saline and titrated to pH 7 using 0.02N sodium hydroxide. The number of equivalents of sodium hydroxide used is a measure of the amount of acid produced. The less sodium hydroxide required, the less gastric acid produced, and the more effective the inhibition.

The compound to be tested is dissolved or suspended in an aqueous solution (containing 0.05% Tween 80) at appropriate concentrations so that oral or i.p. administration of 1 ml per 100 g of rat weight gives the proper dosage. For compounds that are insoluble in water, such may be tested by dissolving in either 0.01N hydrochloric acid (for i.p. dosing) or 3% lactic acid (for oral dosing). In each study, five animals are used per group, and the results compared to those obtained from experimental controls.

According to this test, for example, it has been found that at least 25 percent inhibition of gastric acid secretion, as compared with controls, are obtained at i.p. or oral doses of about 10-100 mg/kg of the subject compounds (I) in base or acid addition salt form.

In addition to antisecretory action, the compounds of formula (I) and salts thereof are active inhibitors of ulcer formation, as demonstrated in acid-induced or stress induced ulcer tests on laboratory animals. For example, the subject compounds (I), in base or salt form, are observed to inhibit the formation of acid-induced ulcers in the pyloric-ligated rat at oral doses of about 10–100 mg/kg body weight by the technique of H. Shay, et al. Gastroenterology, 5, 43 (1945), and I. L. Bonta, Arch. Int. Pharmacodyn., 132, 147 (1961).

According to this procedure, male Sprague-Dawley rats (CFE, 160–180g) are allowed only water ad libitum for 48 hours prior to use and are housed in individual cages. The compound to be tested is administered orally one hour prior to surgical ligation of the pylorus (as described heretofore). After 18 hours, the rats are sacrificed by cervical dislocation; and the stomachs are removed and placed in 10% buffered formalin for one minute. The stomachs are then rinsed with water, blotted and examined for ulcers, which are generally found in the nonglandular, upper half of the stomach. The number of ulcers and the severity thereof are determined. The severity is rated on the basis of the approximate diameter of the ulcer according to the following scale:

| Approximate Diameter (mm) | Score |
|---|---|
| <0.9 | 0.5 |
| 1.0–1.9 | 1 |
| 2.0–2.9 | 2 |
| 3.0–3.9 | 4 |
| >4.0 | 8 |
| Perforation | 16 |

Stomachs found to be free of ulcers, but demonstrating a moderate hyperemia, are scored 0.5 for each area. Perforated ulcers are scored 16. The data is represented as the "ulcer-score," which is the sum of the number of ulcers per stomach plus the severity rating for each ulcer. The average ulcer score for each group of 5 rats is compared to the experimental control value and to the cumulative control value for the percent inhibition at a given dose. A statistical evaluation is made of both sets of data using the Student-t test; the inhibition is considered significant if p < .05 or not significant if p > .05.

The subject 2-pyrrolyl-perimidines are also active in inhibiting the formation of stress-induced stomach ulcers in the cold, restrained rat at oral doses of about 10–100 mg/kg body weight. In this model there is a development of ulcers in the glandular mucosal region of the rat's stomach. The rat has been shown to be a useful model for the study of stress-induced ulcers in humans, which is an important cause of morbidity in a variety of clinical situations [see R. Lambert, Prog. Gastroenteral, 1, 40 (1968); E. Eisman and R. L. Hegman, N. Engl. J. Med., 282, 372 (1920)].

In this procedure, male Wistar rats (140-180 g, Carsworth Farms, CFN) are allowed only water ad libitum for 24 hours prior to testing. One hour after oral administration of test compounds (or vehicle), the rats are immobilized by placing each of them in a tight-fitting wire mesh cylinder (7 inches long × 2 inches in diameter) closed at one end. A piston-like wooden plug is inserted into the open end and is adjusted to the rat size. The plug is held in place with a U-shaped pin, and the tail of the rat (which exits through a hole in the cylinder) is taped to the outside of the cylinder. Immediately upon being restrained, the rats are placed in a room at 4°C for two hours, after which time they are removed from the cylinders and are sacrificed by cervical dislocation. The stomachs are removed, inflated with 5 ml of water and placed in a buffered solution of 10% formalin for one minute, and then rinsed with water. The stomachs are then cut open along the greater curvature, the insides rinsed with water, and pinned open on a cork-board for counting ulcers.

In view of the antiulcer activity of the subject compounds, there is provided herein a method of aiding the prevention and amelioration of ulcers which comprises internally administering to a subject having ulcers an effective ulcer-inhibiting amount of such 2-pyrrolyl-perimidines, in base or acid addition salt form, preferably in admixture with a pharmaceutically acceptable carrier.

To prepare the pharmaceutical compositions of this invention, a 2-pyrrolyl-perimidine (I) or salt thereof is combined as the active ingredient in intimate admixture with a pharmaceutical carrier according to the conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions herein will contain, par dosage unit, e.g., tablet, capsule, powder, injection, teaspoonful and the like from about 10 to about 500 mg of the active ingredient, and, preferably, from about 15 to about 250 mg.

Pharmaceutical compositions exemplified hereinafter illustrate typical unit dosages suitable for internal administration to man or other warm blooded animals for antiulcer purposes.

The compounds of formula (I) may be converted to the corresponding therapeutically active non-toxic acid addition salt form by reaction with an appropriate inorganic acid, such as, for example, hydrochloric, hydrobromic, hydriodic, sulfuric, phosphoric, nitric and the like acids, or with an appropriate organic acid, such as, for example, acetic, propionic, glycolic, lactic, oxalic, malonic, sulfamic, p-toluenesulfonic and the like acids. In turn, the acid addition salts may be converted to the corresponding free base form by conventional treatment with suitable alkali.

The following examples are intended to illustrate, but not to limit, the scope of the present invention.

EXAMPLE I

Capsules 10,000 Hard gelatin capsules, each containing as the active ingredient (A.I.) 50 mg of 2-(2-pyrrolyl)-perimidine HCl, are prepared from the following formulation:

|  | Grams |
| --- | --- |
| A.I. | 500 |
| Lactose | 750 |
| Starch | 250 |
| Talc | 250 |
| Calcium Stearate | 10 |

A uniform mixture of the active and supplementary ingredients is prepared and filled into two-piece hard gelatin capsules.

EXAMPLE II

Tablets 5,000 Compressed tablets, each containing as the active ingredient (A.I.) 10 mg of 2-(N-methyl-2-pyrrolyl)-perimidine, are prepared from the following formulation:

|  | Grams |
| --- | --- |
| A.I. | 50 |
| Starch | 75 |
| Dibasic Calcium phosphate, hydrous | 500 |
| Calcium Stearate | 2.5 |

The finely powdered ingredients are mixed well and are granulated with 10% starch paste. The granulation is dried and compressed into tablets using starch as the disintegrant and calcium stearate as the lubricant.

EXAMPLE III

Injectable

The following formulation provides 1 liter of a parenteral suspension comprising 15 mg of 2-(2-pyrrolyl)-perimidine as the active ingredient per milliliter:

|  | Grams |
| --- | --- |
| A.I. | 15.0 |
| Polysorbate 80 | 2.0 |
| Sodium chloride | 9.0 |
| Sodium Carboxymethyl cellulose | 10.0 |
| Methyl paraben | 1.8 |
| Propyl paraben | 0.2 |
| Water for Injection, U.S.P., q.s. ad | 1 liter |

Dissolve the parabens, sodium chloride, and carboxymethyl cellulose in one-half the total volume of water by heating to 95°C to obtain a clear solution. Filter and autoclave. Dissolve the polysorbate in one-third the total volume of water. Filter and autoclave this second solution. Add sterile A.I. to the second solution and pass it through a sterile colloid mill. To the resulting suspension add the first solution with uniform stirring. Q.s. with sterilized water and stir while filling into sterile vials.

EXAMPLE IV

Oral Suspension

The following formulation provides 5 liters of an oral suspension comprising 100 mg of 2-(N-methyl-2-pyrrolyl)-perimidine as the active ingredient per teaspoonful (5 mls):

|  | Grams |
|---|---|
| A.I. | 100.0 |
| Sucrose | 300.0 |
| Dioctyl sodium sulfosuccinate | 0.5 |
| Bentonite | 22.5 |
| Methyl paraben | 7.5 |
| Propyl paraben | 1.5 |
| Antifoam A.F. Emulsion | 0.15 |
| Propylene glycol | 52.0 |
| FD&C Yellow No. 5 | 0.1 |
| Sodium cyclamate | 50.0 |
| Sodium saccharin | 5.0 |
| Orange flavor | 7.5 |
| Filtered purified water, q.s. ad 5 liters | |

Dissolve the parabens in the propylene glycol and add this solution to a solution of the sodium cyclamate, sodium saccharin and sucrose in half the water. Suspend the bentonite in hot (about 85°C) water and stir for 60 minutes. Add the bentonite solution to the former solution. Dissolve the sulfosuccinate in some water and suspend the A.I. in the resulting solution. Add the Antifoam A.F. Emulsion which has been diluted to a lotion consistency with a minimum amount of water and mix well. Add the latter suspension of A.I. to the former mixture and mix well. Add the FD&C Yellow No. 5 dissolved in a small amount of water. Add the orange flavor, q.s. to volume with water, and stir to a homogeneous mixture. Pass the mixture through a colloid mill and fill into suitable containers.

EXAMPLE V

Capsules 10,000 Hard gelatin capsules, each containing as the active ingredient (A.I.) 400 mg of 2-(2-pyrrolyl)-perimidine HCl, are prepared from the following formulation:

|  | Grams |
|---|---|
| A.I. | 4000 |
| Lactose | 750 |
| Starch | 250 |
| Talc | 250 |
| Calcium Stearate | 10 |

A uniform mixture of the active and supplementary ingredients is prepared and filled into two-piece hard gelatin capsules.

What is claimed is:

1. The method of aiding the prevention and amelioration of stomach ulcers which comprises orally or parenterally administering to a subject having a stomach ulcer an effective stomach ulcer-inhibiting amount of a member selected from the group consisting of a pyrrolyl-substituted perimidine of the formula:

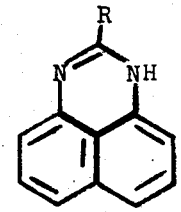

wherein R is a member selected from the group consisting of pyrrolyl and N-methylpyrrolyl, and a pharmaceutically acceptable acid addition salt thereof.

2. The method of aiding the prevention and amelioration of stomach ulcers which comprises orally or parenterally administering to a subject having a stomach ulcer a pharmaceutical composition in dosage unit form comprising per dosage unit from about 10 to about 500 mg of a member selected from the group consisting of a pyrrolyl-substituted perimidine of the formula:

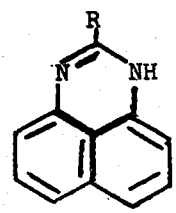

wherein R is a member selected from the group consisting of pyrrolyl and N-methylpyrrolyl, and a pharmaceutically acceptable acid addition salt thereof, in admixture with a pharmaceutically acceptable carrier.

* * * * *

UNITED STATES PATENT AND TRADEMARK OFFICE
CERTIFICATE OF CORRECTION

PATENT NO. : 3,957,993
DATED : May 18, 1976
INVENTOR(S) : Russell J. Taylor, Jr.

It is certified that error appears in the above–identified patent and that said Letters Patent are hereby corrected as shown below:

In Column 3, line 56, "par" should read --- per ---.

Signed and Sealed this fifth Day of July 1977

[SEAL]

Attest:

RUTH C. MASON
Attesting Officer

C. MARSHALL DANN
Commissioner of Patents and Trademarks